(12) United States Patent
Bastide et al.

(10) Patent No.: US 10,942,956 B2
(45) Date of Patent: Mar. 9, 2021

(54) DETECTING MEDICAL FRAUD AND MEDICAL MISUSE USING A SHARED VIRTUAL LEDGER

(71) Applicant: International Business Machines Corporation, Armonk, NY (US)

(72) Inventors: Paul R. Bastide, Littleton, MA (US);
Jonathan Dunne, Mulhuddart (IE);
Liam Harpur, Mulhuddart (IE);
Robert E. Loredo, Boca Raton, FL (US)

(73) Assignee: International Business Machines Corporation, Armonk, NY (US)

( * ) Notice: Subject to any disclaimer, the term of this patent is extended or adjusted under 35 U.S.C. 154(b) by 450 days.

(21) Appl. No.: 15/336,157

(22) Filed: Oct. 27, 2016

(65) Prior Publication Data

US 2018/0121620 A1 May 3, 2018

(51) Int. Cl.
*G16H 20/10* (2018.01)
*H04W 12/12* (2009.01)
*G06F 16/33* (2019.01)

(52) U.S. Cl.
CPC ........... *G06F 16/334* (2019.01); *G16H 20/10* (2018.01); *H04W 12/1206* (2019.01)

(58) Field of Classification Search
CPC ............. G06F 19/328; G06F 17/30675; G06F 19/3456; H04W 12/12
See application file for complete search history.

(56) References Cited

U.S. PATENT DOCUMENTS 5,597,995 A * 1/1997 Williams ............... G06F 19/328
235/375
7,630,908 B1 * 12/2009 Amrien .................. G06Q 50/22
705/3
(Continued)

FOREIGN PATENT DOCUMENTS

WO  WO2015167852 A1  11/2015
WO  WO-2018037148 A1 *  3/2018  ............. G06F 19/00

OTHER PUBLICATIONS

"Pharmacist Help Customers Stop Prescription Drug Abuse", http://allhealthcre.monster.com/training/articles/2886, printed Oct. 27, 2016, pp. 1-3.

(Continued)

*Primary Examiner* — Michael Tomaszewski
*Assistant Examiner* — Mohmad Muqueeth
(74) *Attorney, Agent, or Firm* — Scully, Scott, Murphy & Presser, P.C.; Jared Montanaro, Esq.

(57) ABSTRACT

A system and method of detecting medical fraud using blockchains including receiving a prescription comprising first prescription data from a prescription entry device associated with an prescribing entity, generating a validation code for the prescription based on the first prescription data, adding the validation code to the first prescription data, appending the first prescription data including the validation code to a blockchain, and receiving a query associated with the prescription from a prescription verification device associated with a prescription dispensing entity. The query includes second prescription data. The method further includes comparing the first prescription data to the second prescription data, for example, using pixel comparison, determining based on the comparison that the prescription has been modified, and transmitting to the prescription (Continued)

verification device an indication that the prescription has been modified.

20 Claims, 11 Drawing Sheets

(56) References Cited

U.S. PATENT DOCUMENTS

| | | | |
|---|---|---|---|
| 9,298,877 | B2 | 3/2016 | Hill et al. |
| 2003/0234960 | A1* | 12/2003 | Kaltenbach ............. G06K 5/02 358/3.24 |
| 2005/0113969 | A1* | 5/2005 | Spano, Jr. ........... G06F 19/3462 700/237 |
| 2006/0259330 | A1* | 11/2006 | Schranz ............... G06F 19/328 705/3 |
| 2008/0097786 | A1* | 4/2008 | Sachdeva ............. G06Q 10/00 705/2 |
| 2012/0273564 | A1* | 11/2012 | Mercolino ............... G07D 7/20 235/375 |
| 2014/0173422 | A1 | 6/2014 | Stone et al. |
| 2015/0332283 | A1 | 11/2015 | Witchey |

OTHER PUBLICATIONS

Piper C.,"10 Popular Health Care Provider Fraud Schemes", http://www.acfe.com/article.aspx?id=4294976280, printed Oct. 27, 2016, pp. 1-11.

Wartell J., "Prescription Drug Fraud and Misuse" Guide No. 24 2nd Edition, http://www.popcenter.org/problems/precription_fraud/, printed Oct. 27, 2016, pp. 1-8.

Blockchain (database), https://en.wikipedia.org/wiki/Blockchain, printed Oct. 27, 2016, pp. 1-8.

"Helthcare transaction validation via blockchain proff-of-work, systems and methods", https://www.google.com/patents/US20150332283, printed Oct. 27, 2016, pp. 1-12.

* cited by examiner

DETECTING MEDICAL FRAUD AND MEDICAL MISUSE USING A SHARED VIRTUAL LEDGER

TECHNICAL FIELD

The present disclosure relates to the use of a shared virtual ledger to prevent medical fraud and medical misuse of prescriptions.

BACKGROUND

Health care fraud costs the country tens of billions of dollars a year. National health expenditures in the U.S. reached $2.6 trillion in 2010—17.9 percent of GDP. Over the period of 2015-2021, health spending is projected to grow at an average rate of 6.2 percent annually. With that increase there is an increased likelihood of fraud and fraud comes in many forms.

Given statistics on the number of prescriptions doctors write, doctor shopping may be the prescription fraud tactic with the highest success rate. The Centers for Disease Control and Prevention reports that the number of written prescriptions per office visit increased by 34 percent between 1985 and 2000 alone. Unlike other crimes, however, much prescription fraud goes undetected because it is not a high police priority so very few local agencies systematically track it. Limited awareness and lack of oversight among doctors and pharmacists may also contribute to the problem. Limited education during physician training concerning pain, assessment of addiction liability, and how to use tools to reduce addiction liability also likely contribute to the problem.

Some examples of prescription fraud include over-the-counter (OTC) drug misuse, forging prescriptions, consulting multiple doctors to obtain prescriptions ("doctor shopping"), obtaining prescribed drugs illegally through the Internet, acquiring drugs that were legally prescribed to family members or friends, or altering prescriptions to increase the quantity.

For example, customers abusing drugs may try to obtain refills earlier than prescribed, fill a prescription for the same medication using different physicians or demand a prescription be filled on the same day that it brought in to a pharmacy. It is often difficult to detect customers who visit multiple pharmacies to obtain the same medication, especially on the same day. In one example, a relief worker who worked at several pharmacies in Pierre, S. Dak. recognized customers who had been in the other pharmacies where she was also filling in. The relief worker, "had seen someone at one pharmacy one day, and then I saw them at another pharmacy." The relief worked then checked with the other pharmacies and alerted the department of health about the potential fraud.

Once a pharmacist notices a potential problem or warning sign that a customer may be involved in fraud or drug abuse, the pharmacist may collect more clues by contacting other pharmacies to ask if the customer has been filling prescriptions there as well. If the evidence suggests drug abuse, the first step is usually to contact the customer's doctor."

Further complicating the problem is the fact that prescriptions often come in several different forms. For example, a prescription may be for a single use or may be for multi-use. Often the different forms of prescription are also presented on the same prescription sheet where, for example, the only difference may be a number of refills, an expiration date, or other similar information. This makes detection of fraud or drug abuse a challenge for the individual and the heath care system where it may be easy to modify the prescription in a plausible manner to increase the number of pills, number of refills, extend the expiration date, or other similar modifications to the prescription that may be difficult to catch.

BRIEF SUMMARY

The system, method, and computer program product described herein provide a mechanism for tracking prescriptions from creation through dispensation in a manner that reduces fraudulent transactions. In an aspect of the present disclosure, a method is disclosed. The method includes receiving a prescription comprising first prescription data from a prescription entry device associated with an prescribing entity, generating a validation code for the prescription based on the first prescription data, adding the validation code to the first prescription data, appending the first prescription data including the validation code to a blockchain, and receiving a query associated with the prescription from a prescription verification device associated with a prescription dispensing entity. The query includes second prescription data including the validation code. The method further includes comparing the first prescription data to the second prescription data, determining based on the comparison that the prescription has been modified, and transmitting to the prescription verification device an indication that the prescription has been modified.

In aspects of the present disclosure apparatus, systems, and computer program products in accordance with the above aspect may also be provided.

BRIEF DESCRIPTION OF THE DRAWINGS

The details of the present disclosure, both as to its structure and operation, can best be understood by referring to the accompanying drawings, in which like reference numbers and designations refer to like elements.

DETAILED DESCRIPTION

The present disclosure provides methods and systems to combat prescription fraud and drug abuse through the use of a shared ledger system.

The shared ledger system may be accessible to any medical professional or drug providing entity including, for example, physicians or other healthcare professionals, doctor's offices, hospitals, pharmacies, mail-order prescription companies or any other company that interfaces with the creation of a prescription or dispensation of drugs based on a prescription.

In some aspects, the shared ledger system may be immutable, where, for example, once an entry has been added to the shared ledger system, the entry may not be changed by any party with access to the shared ledger system. As an example, the shared ledger system may be implemented by blockchain technology.

Blockchain technology was developed as a way of providing a publicly transparent and decentralized ledger that is configured to track and store digital transactions in a publicly verifiable, secure, and hardened manner to prevent tampering or revision.

A typical blockchain includes three primary functions: read, write, and validate. For example, a user of the blockchain must have the ability to read the data that resides on the blockchain. A user of the blockchain must also have the ability to write, e.g. append, data to the blockchain. Every write operation starts out as a proposed transaction that is posted on the network. The proposed transaction may not always be valid, for example, it may be malformed (syntax errors), or it may constitute an attempt to perform a task for which the submitter is not authorized. Validation refers to filtering out invalid transactions and then deciding on the exact order for the remaining, valid, transactions to be appended to the blockchain as part of a new block.

Once ordered, the transactions are packaged into a new block, and the new block is voted on by the validator nodes associated with the blockchain to determine whether to add the new block to the blockchain. If a consensus to add the new block is reached, e.g., a threshold number of "for" votes, the new block may be appended to the blockchain. Each new block that is appended to the blockchain also includes a hash of the previous block. Accordingly, as each new block is added, the security and integrity of the entire blockchain is further enhanced. It is important to note that once data is written to the blockchain, for example, once a block including a set of transactions has been appended to the blockchain, that data can no longer be altered or modified. In a typical blockchain, the anonymity of the users is protected through the use of pseudonyms and the transaction data itself is protected through the use of cryptography, e.g., via the use of hash codes.

Figure 1:
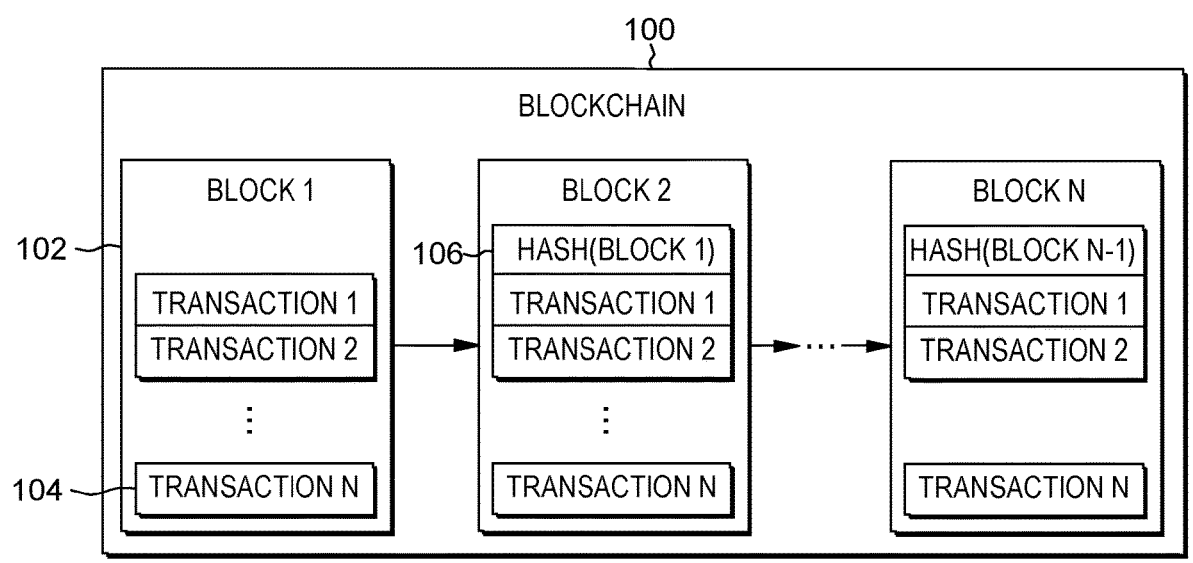
FIG. 1 is a system diagram illustrating a blockchain in accordance with an aspect of the present disclosure.

With reference now to FIG. 1, a blockchain 100 includes a plurality of data blocks 102. Each data block 102 is a data structure that includes data representing transactions 104, for example, prescriptions, queries to the blockchain regarding a prescription, or any other transaction related to a prescription. As described above, as new transactions 104 are submitted to the blockchain 100 and validated by validator nodes, additional data blocks 102 are generated by the validator nodes and appended to the blockchain 100. Each new data block 102 includes a set of validated transactions 104 and a hash 106 of the content of the immediately previous data block 102. For example, data block "2" includes a hash of the content of block "1", block "n" includes a hash of the content of block "n–1", etc. Some non-limiting examples of blockchains include Bitcoin®, Ethereum®, OpenLedger™, or other similar blockchains. In some aspects, the hashes may be generated by the validator nodes 300 as the validator nodes generate new blocks for addition to blockchain 100.

Figure 2:
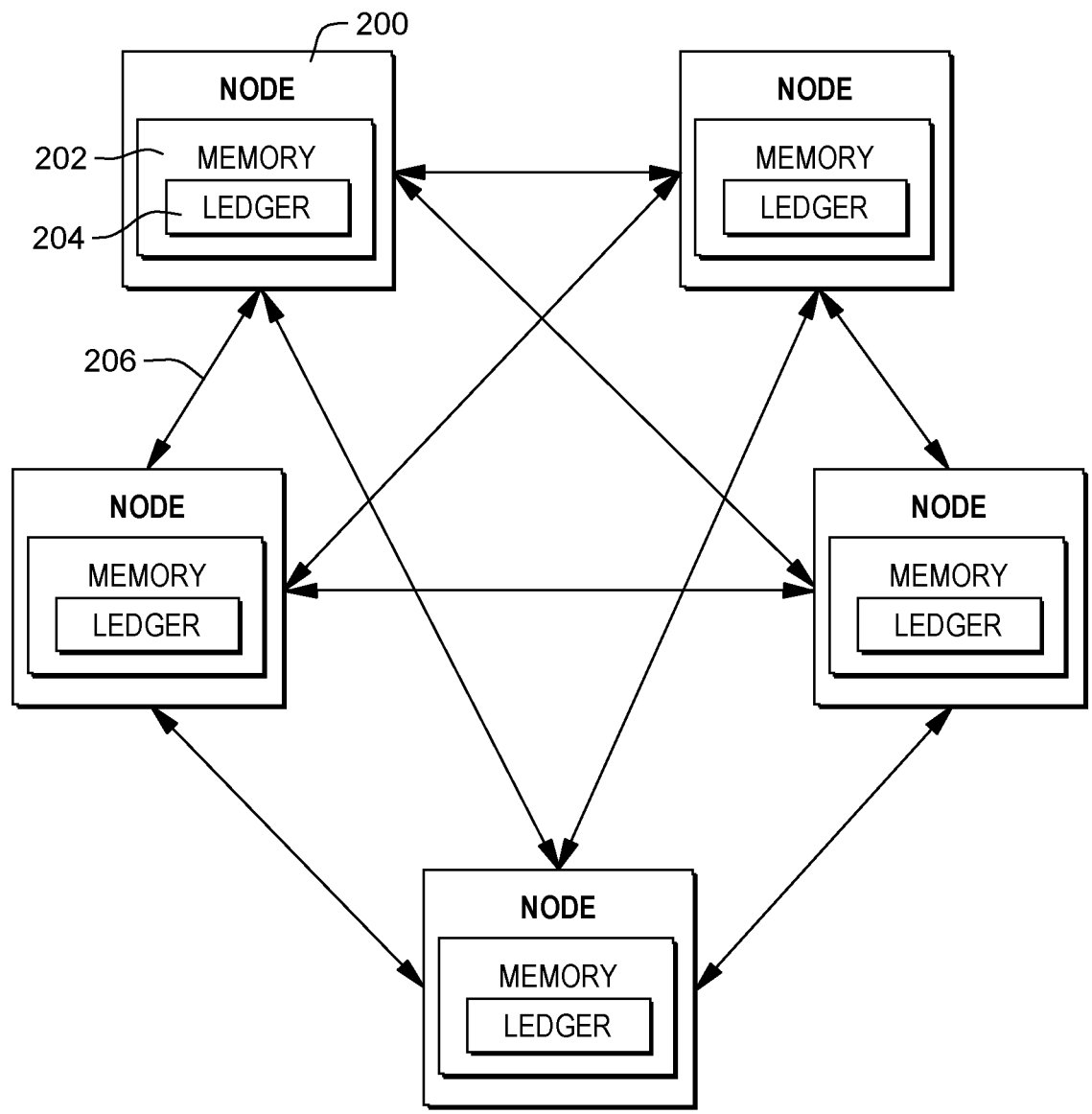
FIG. 2 is a system diagram illustrating nodes associated with the blockchain of FIG. 1 and storing the ledger of the blockchain of FIG. 1 in accordance with an aspect of the present disclosure.

With reference now to FIG. 2, in some aspects, blockchain 100 is stored in a decentralized manner on a plurality of nodes 200, e.g., computing devices located in one or more networks. Nodes 200 may each include a memory 202 that stores at least a portion of a ledger 204 of blockchain 100. Ledger 204 includes any data blocks 102 that have been validated and added to the blockchain 100. In some aspects, every node 200 may store the entire ledger 204. In some aspects, each node 200 may store a portion of ledger 204. In some aspects, some or all of blockchain 100 may be stored in a centralized manner. Nodes 200 may communicate with one another via communication pathways 206, e.g., wired or wireless connections, over the internet, etc. to transmit and receive data related to ledger 204. For example, as new data blocks 102 are added to ledger 204, nodes 200 may communicate or share the new data blocks 102 via communication pathways 206. In some aspects, some or all of nodes 200 may be operated by a healthcare provider, a group of healthcare providers, a pharmacy, a group of pharmacies, an insurance provider, a group of insurance providers, or any other entity that may have a stake in monitoring prescription usage. In some aspects, some or all of nodes 200 may be anonymous and unrelated to the creators or users of the prescription.

Figure 3:
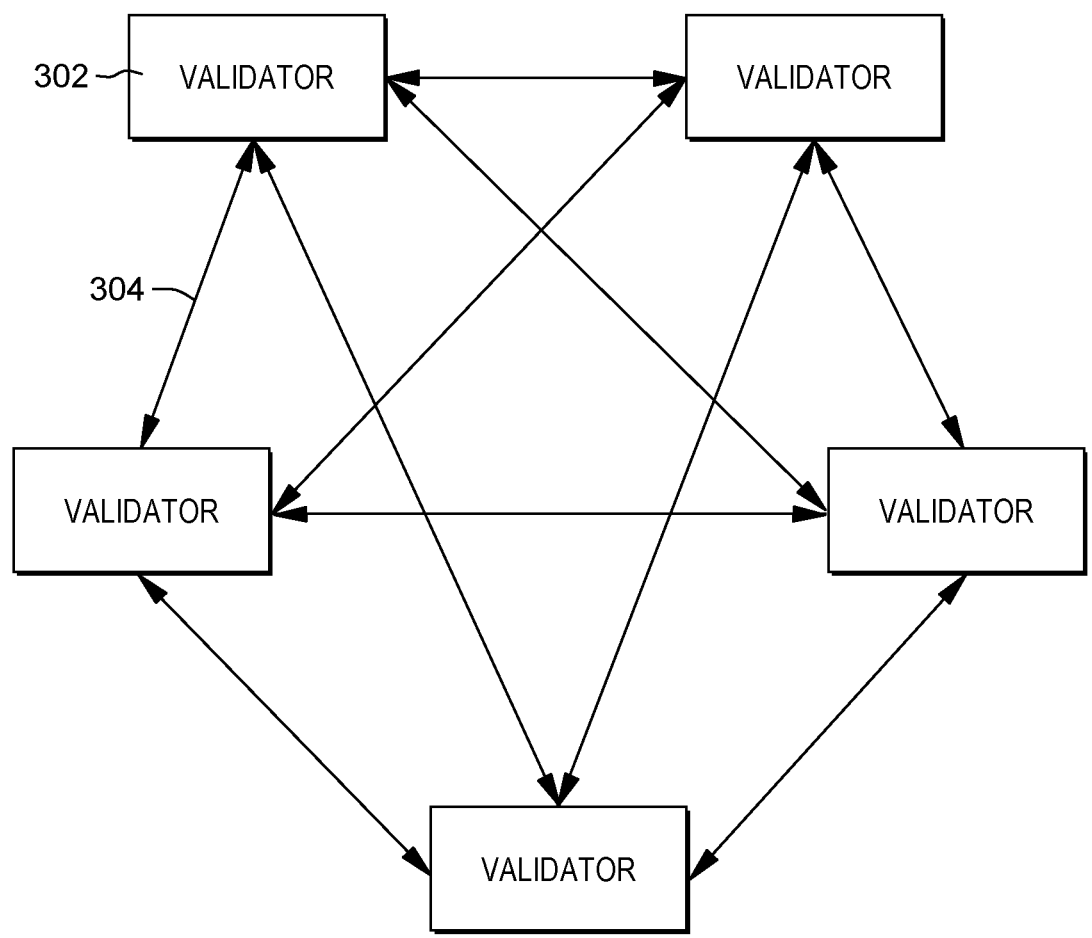
FIG. 3 is a system diagram illustrating validator nodes associated with the blockchain of FIG. 1 in accordance with an aspect of the present disclosure.

With reference now to FIG. 3, any transactions 104 submitted to blockchain 100 are validated by a set of validator nodes 300 associated with blockchain 100. For example, transactions 104 may be transmitted to one or more of the validator nodes 300 and may be shared between the validator nodes 300 for validation and consensus. Each validator node 302 determines whether a transaction 104 is valid and whether the transaction 104 complies with the rules of the blockchain 100. The validator node 302 adds a plurality of the validated transactions 104 to a data block 102 and submits the data block 102 for consensus by all or some of the other validator nodes. The other validator nodes 302 then vote "for" or "against" appending the data block 102 containing the transactions 104 to the blockchain 100. A consensus of the set of validator nodes 300, e.g., a threshold number of identical votes "for" or "against", is required to allow or deny the data block 102 to be appended to the blockchain 100. In some aspects, one or more of nodes 200 may also be validator nodes 302. In some aspects, nodes 200 that are not validator nodes 302 may perform processing such as, for example, receiving transaction submissions, providing member services, handling application programming interface (API) requests from users, or other similar functions. In this manner, the processing power of the validator nodes 302 may be preserved for generating new blocks, reaching consensus, and monitoring the other validator nodes 302. Validator nodes 302 may communicate with one another via communication pathways 304, e.g., wired or wireless connections, over the internet, etc., to transmit and receive data. For example, as new data blocks 102 are generated by validator nodes 302, validator nodes 302 may communicate or share the new data blocks 102 and transmit and receive consensus messages via communication pathways 304. In some aspects, some or all of validator nodes 302 may be operated by a healthcare provider, a group of healthcare providers, a pharmacy, a group of pharmacies, an insurance provider, a group of insurance providers, or any other entity that may have a stake in monitoring prescription usage. In some aspects, some or all of validator nodes 302 may be anonymous and unrelated to the creators or users of the prescription.

In some aspects, the users of the shared ledger system may be known and may provide contact information such that when new transactions or queries related to a particular prescription are received from a new user, e.g., a pharmacy, the new user may easily identify the prior user, e.g., a physician or other medical personnel, and may contact the prior user when a potential case of fraud or drug abuse is detected.

In an aspect, any prescription related activities may be tracked and logged as transactions for appending to the blockchain implementing the shared ledger system. For example, the creation of a new prescription by a physician or other healthcare professional, the modification of a prescription by the physician or other healthcare professional, the dispensation of a prescription by a pharmacy, queries to the shared ledger about a prescription by a physician, other healthcare professional, pharmacy, or other entity, or other similar transactions or activities related to a prescription may be appended to the shared ledger.

Figure 4:
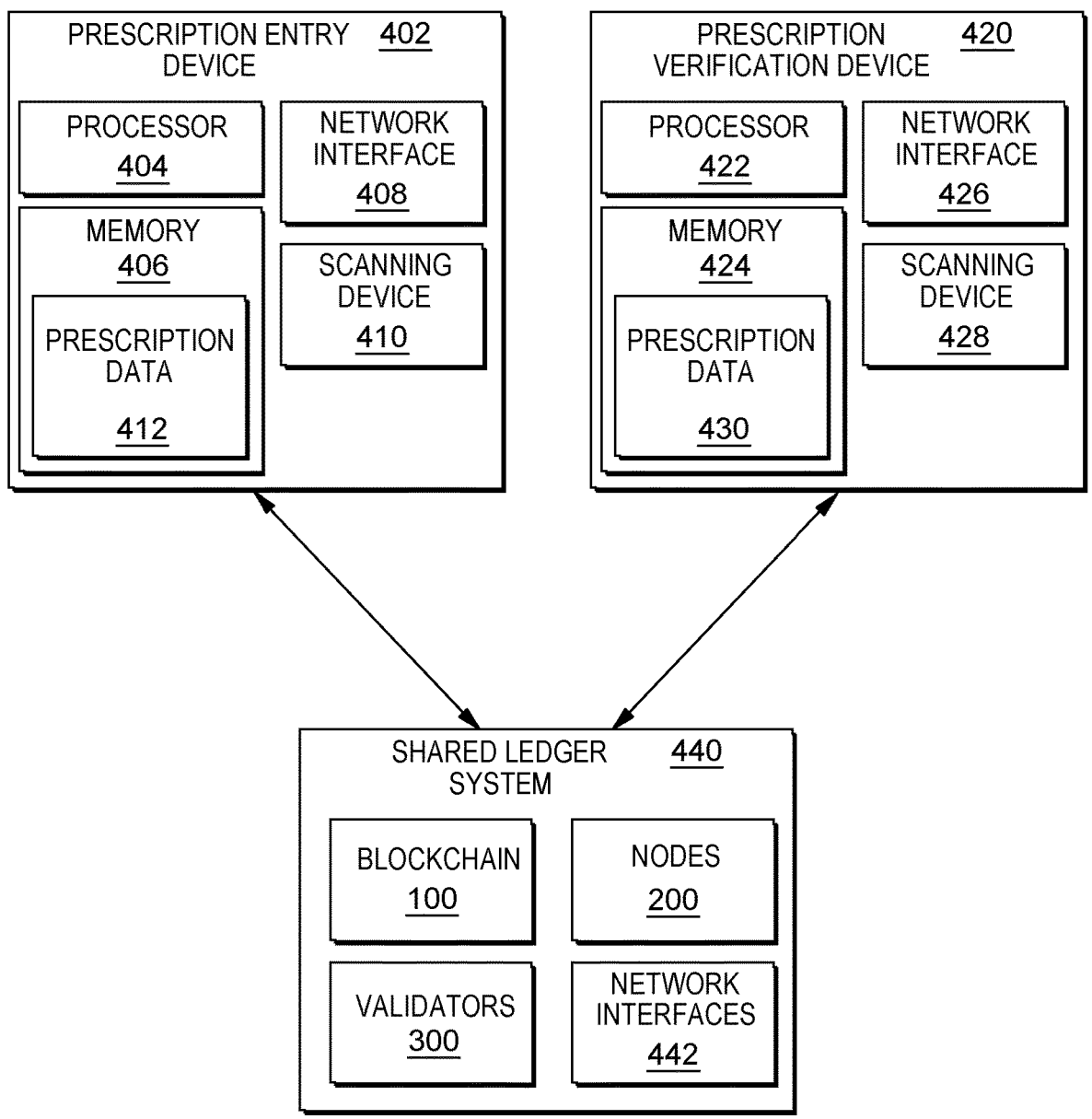
FIG. 4 is a system diagram illustrating components of a system in accordance with an aspect of the present disclosure.

With reference now to FIG. 4, a system 400 is illustrated. System 400 includes a prescription entry device 402, a prescription validation device 420, and shared ledger system 440. Shared ledger system 440 includes blockchain 100, nodes 200, validators 300, and network interface 442 associated with each of blockchain 100, nodes 200 and validators 300 and configured to allow communication with and between blockchain 100, nodes 200 and validators 300 and any other computing device via wired or wireless connections, the internet, or any other method of communication.

Prescription entry device 402 includes at least one processor 404, memory 406, and a network interface 408. In some aspects, prescription entry device 402 may be provided to physicians, other healthcare professionals, hospitals, or other entities that create prescriptions. For example, prescription entry device 402 may be a computing device associated with or owned by the physician, other healthcare professional, hospital, or other entity. In some aspects, prescription entry device 402 also include a scanning device 410 that is configured to digitally scan prescriptions and generate prescription data 412 based on the scanned prescriptions for storage in memory 406. In some aspects, prescription data 412 for each prescription may include an image of the prescription. In some aspects, scanning device 410 and prescription entry device 402 may be separate devices that are in communication via network interface 408.

Memory 406 may include instructions, software, and/or programs that may be executed by processor 402. Memory 406 may also store prescription data 412 generated by scanning device 410.

Network interface 408 may be configured to communicate with other computing devices, the internet, the cloud, or any other device, via wired or wireless technology. For example, network interface 408 may be configured to communicate with shared ledger system 440 via one or more network interfaces 442 of shared ledger system 440.

Scanning device 410 may be any device that is capable of generating a digital image based on a hardcopy. Example scanning devices 410 may include multi-function printers, stand alone scanning devices, digital cameras, smart phones, other smart devices, or any other scanning device that is capable of capturing a digital image and/or perform optical character recognition (OCR) of a prescription and generating prescription data from the digital image.

Figure 5:
FIG. 5 is a diagram illustrating typical prescription in accordance with an embodiment of the present disclosure.

Prescription entry device 402 may be used by a physician, other healthcare professional, hospital, or other entity that is authorized to issue prescriptions for patients. For example, with reference now to FIG. 5, a physician may "write" a prescription 502 for a patient. Prescription 502 may include prescriber information 504, e.g., a prescribing entity such as a doctor's office, hospital, or other entity, a list of physicians or other healthcare professionals, or other similar prescriber information. Prescription 502 may include a patient name 506, a prescription issue date 508, drug information 510 (e.g., drug type 512, dosage 514 and instructions 516) a quantity 518 to be dispensed per refill, a number of refills 520, and a physician's signature 522. In some aspects, where the drug is a controlled substance, the prescription may also include additional information where required by the government, for example, the physicians DEA number (not shown).

In some aspects, prescription 502 may be a hardcopy, for example, a piece of paper, card stock, or other material, and the physician may physically fill in the fields of the prescription 502 as necessary to complete the prescription 502 by hand. For example, the physician may physically write the patient name 506, prescription issue date 508, drug information 510, quantity 518 per refill, number of refills 520, on the prescription 502 and may sign the prescription 502 with a signature 522. The hardcopy of prescription 502 may then be scanned by scanning device 410 to generate prescription data 412 which may be stored in memory 406. In some aspects, scanning of the hardcopy of prescription 502 by scanning device 410 may include generating a digital image 600 (FIG. 6) of prescription 502.

Figure 6:
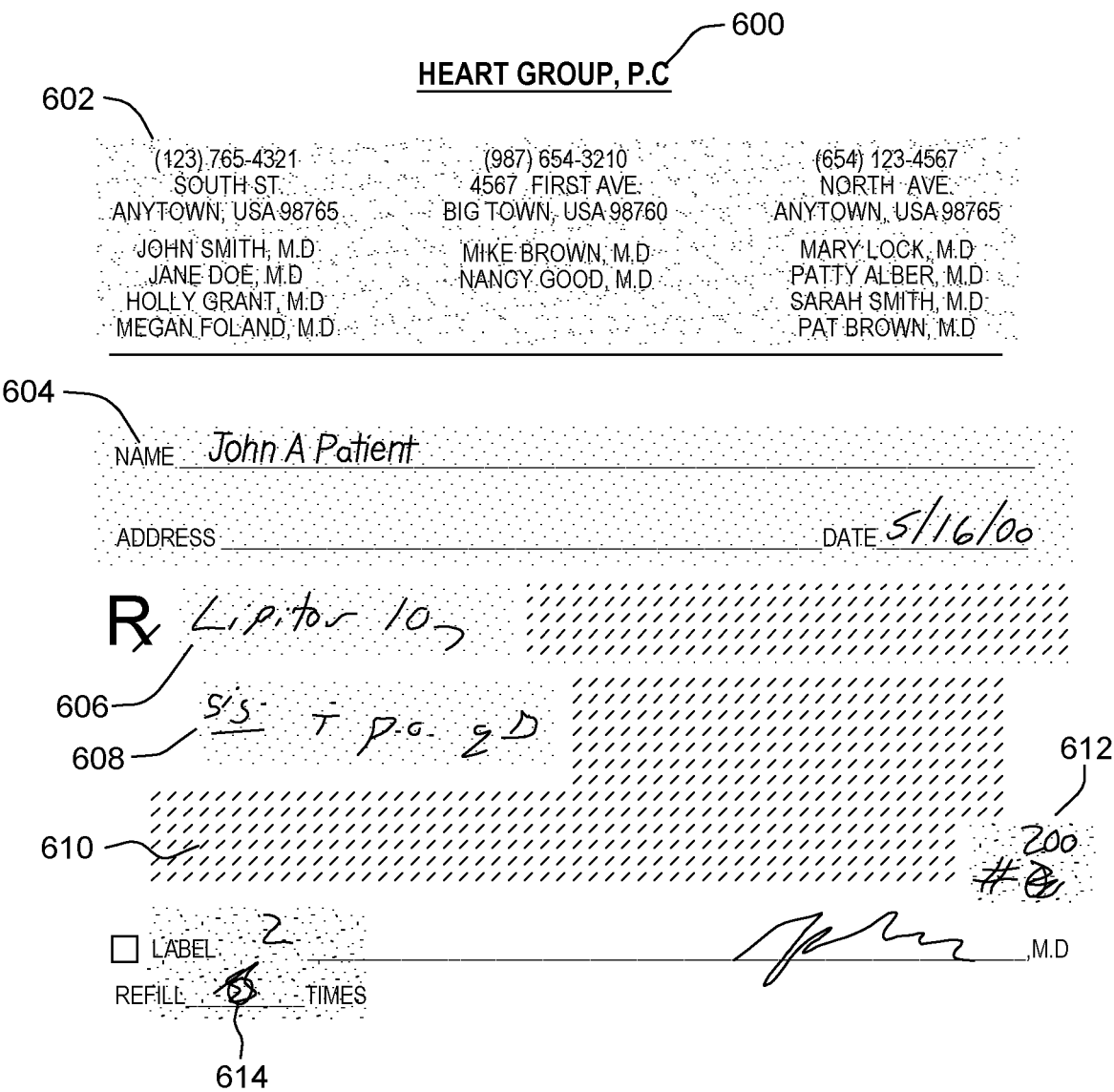
FIG. 6 is a diagram illustrating an image of a prescription including the identification of key regions in accordance with an embodiment of the present disclosure.

In some aspects, the physician may generate prescription 502 using prescription entry device 402 without generating a hardcopy of the prescription 502. For example, the physician may fill in each field of prescription 502 digitally and the prescription data 412 for the digital prescription 502 may be stored directly in memory 406 without any need to scan the prescription 502 with scanning device 410. The filled in version of the prescription 502 may also be stored as part of the prescription data 412 as a digital image 600 (FIG. 6). In some aspects, once the prescription 502 has been completed digitally, the physician may print the prescription 502 to a hardcopy, e.g., by a printing device (not shown) associated with prescription entry device 402 and may provide the prescription to the patient.

In some aspects, a validation code, e.g., a hash, of prescription 502 or prescription data 412 may be generated. In some aspects, the validation code may, for example, be generated based on the information entered into the prescription 502 by the physician or other medical personnel. For example, image processing may be performed on the prescription data 412 to identify any text in the prescription 502 and the validation code may be based on the identified text. In some aspects, the validation code may be generated based on, for example, the digital data that represents the prescription 502. In some aspects, the validation code may be generated based on the pixel values that form the image 600 of prescription 502 stored in the prescription data 412. In some aspects, the validation code may be a hash of a file stored on prescription entry device 402 that contains the prescription data 412. For example, the validation code may be a hash of the prescription image file. An example of a validation code for prescription 502 may include "98770778965214190371 Timestamp: 2016-02-29 13:50:17 UST".

In some aspects, the validation code may be printed on the hardcopy of the prescription 502, for example, by a printing device (not shown) associated with prescription entry device 402. In some aspects, for example, where the physician has handwritten the patient and drug information into the fields of the prescription 502, the physician may be provided with the validation code by prescription entry device 402 and may manually write the validation code on the prescription for later use by a pharmacy or other entity that will dispense the prescription.

In some aspects, the validation code may be generated by shared ledger system 440 at a time when the prescription data 412 is submitted by prescription entry device 402, e.g., via network interfaces 408 and 442, as a transaction for addition to blockchain 100. For example, one or more nodes 200 or validator nodes 302 may generate the validation code when the prescription data 412 is received from prescription entry device and may add the validation code to the prescription data 412 prior to appending the prescription data 412 to a block for addition to the blockchain 100.

Once prescription data 412 for a prescription 502 has been submitted to shared ledger system 440 and a validation code has been generated and added to the prescription data 412, prescription data 412 may validated and added to a new block by a validator node 302 (FIG. 3) of shared ledger system 440. The validators 300 may then reach a consensus and add the new block containing the prescription data 412 to the blockchain 100. In some aspects, only prescriptions received from verified prescribers, e.g., those using prescription entry devices 402 may be validated for addition to blockchain 100. For example, if a prescription is received from a non-verified device, shared ledger system 440 may deny entry of the prescription to blockchain 100. In some aspects, all or part of the prescription data 412 may be encrypted when submitted for addition to blockchain 100 to protect patient privacy, for example, by prescription entry device 402 or by shared ledger system 440. In some aspects, an image of the prescription may be stored separately from the blockchain, for example, in a separate database, and the prescription data 412 stored on the blockchain may include a link, e.g., a URL link, pointing to the prescription image.

In some aspects, prescription data 412 may be checked against other prescriptions already added to blockchain 100. For example, the validator node 302 may determine whether there is already an active prescription for the listed patient for the same medication. If such a prescription exists, shared ledger system 440 may notify the prescribing physician, e.g., via prescription entry device 402 and indicate that the prescribing physician should manually verify the existence of the prior active prescription. For example, the prior active prescription that is already appended to blockchain 100 may include identification or contact information for a prescribing physician that may be used to verify whether the patient has already received a prescription for the same medication from another physician. This verification may be used to prevent doctor shopping where, for example, a patient may receive separate prescriptions for the same medication from more than one physician.

In some aspects, a physician or other medical personnel may wish to update or modify a prescription 502 after the prescription data 412 has been added to the blockchain 100. In this case, for example, the physician may make the modification on the hardcopy of the prescription 502 and may re-scan the hardcopy using scanning device 410 to generate and store new prescription data 412 in memory 406. In some aspects, the physician may make the modification directly in the prescription data 412 stored in memory 406. Once the modification has been made, a new validation code may be generated based on the modified prescription data and the modified prescription may be submitted to shared ledger system 440 for entry into the blockchain 100 as a modification transaction. In some aspects, the modified prescription data may also include the validation code of the original transaction including prescription data 412 as a reference. In some aspects, once a modification of a prescription has been received by shared ledger system 440, the original prescription may be de-activated where, for example, any attempted use of an unmodified version of the prescription may result in an indication or warning that the unmodified version is no longer available for dispensation. For example, the prescription may be de-activated by submitting a deactivation transaction to shared ledger system 440 for addition to blockchain 100. The de-activation transaction may specify that the prescription is de-activated and may prevent any future use of the prescription unless the prescription is re-activated, e.g., by the submission of a re-activation transaction by prescription entry device 402 to shared ledger system 440.

In some aspects, shared ledger system 440 may verify that the modified prescription data 412 is received from the same physician or source as the original prescription data 412. If the source is the same, the modification may be accepted and added to blockchain 100. If the source is not the same, shared ledger system 440 may deny entry of the modification to blockchain 100. This may prevent a non prescribing entity, or the wrong prescribing entity from submitting a modification to a prescription that was not originally issued by that entity. For example, in some aspects, each prescription entry device 402 may be pre-verified by shared ledger system 440 and may include or append a pre-verified source identifier to the prescription data 412 submitted to shared ledger system 440. This source identifier may then be used later by shared ledger system 440 to verify the source of the modification to the prescription as the source of the originally submitted prescription.

Referring again to FIG. 4, prescription verification device 420 may include features similar to those found in prescription entry device 402. For example, prescription verification device 420 includes a processor 422, memory 424, network interface 426 similar to those found in prescription entry device 402. In some aspects, prescription verification device 420 may be provided to pharmacies, hospitals, or other similar entities that receive and dispense prescriptions. For example, prescription verification device 420 may be a computing device associated with or owned by a pharmacy, hospital, or other similar entity. In some aspects, prescription verification device 420 may also include a scanning device 428 that is configured to digitally scan prescriptions 502 and generate prescription data 430 based on the scanned prescriptions for storage in memory 424 in a similar manner to that described above with reference to scanning device 410. In some aspects, prescription data 430 for each prescription 502 may include an image 600 (FIG. 6) of the prescription 502. In some aspects, scanning device 428 and prescription verification device 420 may be separate devices that are in communication via network interface 426.

In some aspects, for example, a pharmacist or other medication dispenser may use prescription verification device 420 to verify the authenticity of a prescription received from a customer. For example, the pharmacist may use prescription verification device 420 to query shared ledger system 440 to determine if the prescription received from the customer is present on the shared ledger, and may verify the authenticity of the prescription based on the prescription data 412 that has been appended to blockchain 100. For example, the pharmacist may compare the validation code printed on the prescription to the validation code found in the prescription data 412 appended to blockchain 100. In some aspects, the prescription 502 received from the customer may be scanned in by scanning device 428 in a similar manner to that described above with reference to scanning device 410, a new validation code may be generated for the scanned prescription and the new validation code may be compared to the validation code found in the prescription data 412 appended to blockchain 100.

In some aspects, for example, a digital image of the prescription generated by the prescription verification device 420 may be compared to a digital image of the prescription generated by prescription entry device 402. For example, the digital image of the prescription generated by the prescription entry device 402 may be stored with prescription data 412 on blockchain 100 or in a separate database associated with blockchain 100 and may be downloaded by prescription verification device 420 for comparison to the digital image of the prescription generated by prescription verification device 420. In some aspects, for example, the prescription verification device 420 may compare the digital images using pixel comparison techniques and may set a maximum difference threshold for the pixel comparison. For example, a non-limiting maximum difference threshold between the digital images of the prescription may be set at 3%, e.g., the pixels of the digital images of the prescription may differ by no more than 3%. In some aspects, a maximum difference threshold may also or alternatively be defined separately for each key region of the prescription, e.g., 3% for a first key region, 1% for a second key region, 2% for a third key region, 30% for a fourth key region, etc.

In some aspects, the pixel comparison results for each of the key regions may be combined and compared to a total maximum difference threshold to determine whether the prescription has been modified. For example, if the total maximum difference threshold for the prescription is 5%, a first key region has a pixel difference of 2% and a second key region has a pixel difference of 3%, the prescription may be determined to have been modified. In another example, if the individual regions each had a 1% difference but cumulatively added up to a 5% difference, a modification may be determined even though the maximum difference threshold for each key region may not have been triggered. In some aspects, the key regions may have weightings where, for example, key regions related to pill count, number of refills, etc. may have a higher weight than key regions related to the doctor's name or office.

The maximum difference thresholds for the comparison may be pre-determined in advance, may be set by a user of the prescription verification device 420, may be set by a user of the prescription entry device 402, or by any other user of the system. For example, the maximum difference thresholds may be set by a government entity, medical personnel, or other entity based on data that indicates which key regions of the prescription or how much of the prescription is typically changed in the case of a fraudulent prescription. Examples of key regions are described in more detail below with reference to FIG. 6.

In some aspects, whenever a pharmacy receives a prescription from a customer, a query or check-in may be submitted to the shared ledger system 440 for the prescription to determine whether the prescription is valid. The query may be submitted as a query transaction that may be added to blockchain 100. For example, every time a query is submitted for a particular prescription, the query may be added to blockchain 100 as a transaction such that all future queries will receive a notification that the prescription has been previously queried. In some aspects, the query transaction may include, for example, an identification of the querying entity, a timestamp of the query, a location of the query, or any other information that may be relevant to determining whether a fraudulent use of a prescription occurred. For example, if a query for a particular prescription has been submitted from three different pharmacies in the same area on the same day, this may be a red flag that fraud is being attempted by a customer since it appears that the customer may have tried to fill the same prescription in each the three different pharmacies. In some aspects, once a pre-defined threshold number of queries have been received by shared ledger system 440 for a particular prescription, shared ledger system 440 may indicate to a pharmacist or other entity via prescription verification device 420 that manual validation of the prescription is required, e.g., by contacting the prescribing physician directly.

In some aspects, each time a prescription 502 is filled by a pharmacy or other entity, the pharmacy or other entity may submit a fill transaction for that prescription 502 to shared ledger system 440 for addition to blockchain 100. Each fill transaction may indicate, for example, that the prescription 502 has been filled once. In some aspects, each fill transaction may indicate how many refills remain. Any queries for the prescription will then return a result indicating how many fill transactions have been appended to the blockchain 100 for that prescription 502, allowing the pharmacist to know whether the number of refills value on the prescription has been modified.

In some aspects, once the prescription has been filled a final time, the pharmacist may submit a deactivation transaction to shared ledger system 440, or shared ledger system 440 may generate a deactivation transaction that may be appended to blockchain 100 to indicate that the prescription 502 is no longer active in blockchain 100. For example, any further attempted transactions submitted to shared ledger system 440 based on the deactivated prescription may result in the transmission of a warning to the pharmacy and/or physician that submitted the transaction indicating that the customer has attempted to use the deactivated prescription.

In some aspects, prescription entry device 402 or prescription verification device 420 may be configured to analyze the prescription data 412 to identify key regions of the prescription 502. For example, prescription entry device 402 or prescription validation device 420 may perform image processing on the image 600 (FIG. 6) of prescription 502 that is stored as part of prescription data 412 to identify key regions of prescription 502 as illustrated, for example, in FIG. 6. Example key regions may include a prescriber information region 602, a patient information region 604, a drug information region 606, a patient instructions region 608, an empty space region 610, a quantity region 612, and a refill region 614. In some aspects, one or more of the regions may be combined to form a single region. Each key region may be associated with a predetermine level of risk where, for example, modifications to a first region, e.g., prescriber information, may have a lower risk of fraud than modifications to a second region, e.g., quantity region 612 or refill region 614. For example, a prescription 502 provided by a customer may be damaged or dirtied in a region where there is a low risk of fraud, e.g., prescriber information region 602. When prescription verification device 420 is used to query to blockchain 100 for the prescription, the result of the query may indicate that the prescription 502 has been modified due to the damage or dirtying. Because the modification or damage is in a region having a low risk of fraud, however, the query may still return an indication that the prescription is acceptable for dispensation. In contrast, if the damage or dirtying is in a high risk region, e.g., quantity region 612 or refill region 614, which may cause the unnecessary dispensation of additional drugs to the customer, the query to blockchain 100 may return an indication that it is not acceptable to dispense the prescription since there may be a modification to the prescription. In this case, the query may indicate that the pharmacist should contact the prescribing doctor prior to dispending medication according to the prescription.

In some aspects, the risk level of each region may be predetermined, for example, by the prescribing physician or other medical personnel, hospital, pharmacy, or other entity associated with the prescriptions. In some aspects, the risk level of each region may be pre-defined according to government statute, regulation, rules or guidelines. In some aspects, the risk level of each region may be based on the type of prescription, for example, prescriptions where refills or quantity are often fraudulently modified or easily modified may have a higher risk level for quantity region 612 or refill region 614 than others. In another example, prescriptions for a particular drug that has a similar name to another, more desirable, drug may have a drug information region 606 that has a higher risk level since there is an increased risk of a change or modification to the name of the drug by a customer.

In some aspects, the risk level of each key region may be identified by a color, shading, or other indication in image 600 of prescription data 412. For example, prescriber information region 602 may have a green color, indicating a low risk level, patient information region 604, drug information region 606, and patient instructions region 608 may have a pink color indicating a high risk level, empty space region 610 may have a yellow color indicating a moderate risk level (e.g., a risk that a patient will fill in additional information that was not included in the original prescription 502), and quantity region 612 and refill region 614 may have a beige color indicating a moderate to high risk level. Although each key region is described with respect to a particular color, it is contemplated that any other color or pattern may be used to indicate the risk levels for each key region.

In some aspects, the risk level associated with each key region may be associated with a weighted value where, for example, each modification to a key region having a low risk level, e.g., prescriber information region 602 may have a weighted value of 0.1, each modification to a key region having a moderate risk level, e.g., empty space region 610, may have a weighted value of 0.25, each modification to a key region having a moderate to high risk level, e.g., quantity region 612 and refill region 614, may have a weighted value of 0.5, and each modification to a key region having a high risk level, e.g., patient information region 604, drug information region 606, and patient instructions region 608, may have a weighted value of 0.75. Although example weighted values are provided here, it is contemplated that the weighted values associated with each key region may be any other value and may be adjusted or determined, for example, by a prescribing physician, pharmacy, medical professional, hospital, government entity, or any other entity associated with shared ledger system 440. For example, the weighted values for each key region may be updated according to the level of fraud found in that key region. For example, if it is found that there is an increased amount of fraud in the quantity region 612, the weighted value for the quantity region may be increased accordingly.

In some aspects, each detected modification may be assigned the weighted value of the associated key region in which the modification occurred. For example, if three modifications are detected in the prescriber information region 602, each of the three modifications may be assigned a weighted value of 0.1. The weighted values of each modification may then be combined and compared a pre-determine risk threshold. For example, the weighted values of the three modifications in the prescriber information region 602 may be combined to a value of 0.3 and may be compared to a pre-determined risk threshold. In some aspects, for example, the predetermined risk threshold may be 0.75. As can be appreciated, the example combined value of 0.3 is less than the risk threshold of 0.75 so the threshold has not been met and no warning, or a minor warning, may be issued for the prescription by shared ledger system 440.

In another example, a modification is detected in the refill region 614 in addition to the three modifications in the prescriber information region 602. In this example, the three modifications in the prescriber information region 602 have a combined value of 0.3 whole the single modification to the refill region 614 has a value of 0.5. Combining these values results in a value of 0.8, 0.05 above the pre-determined risk threshold of 0.75. In this case, shared ledger system 440 may notify the pharmacist that the prescription has been modified beyond the pre-determined risk threshold and therefore that manual verification of the prescription is required. In some aspects, the pre-determined risk threshold may be set by the prescribing physician or other medical personnel, by a pharmacy, by a hospital, by the government, or by any other entity associated with shared ledger system 440.

In some aspects, each individual patient, family of patients, etc. may have their own associated blockchain 100 where, for example, the blockchain 100 may only include prescriptions associated with those patients, families, etc. This may make it easier for a pharmacy and/or physician to review the prescription history when a warning is issued. In addition, if a person that is not associated with the prescription on the blockchain 100 attempts to use the prescription, this may also result in the issuance of a warning by shared ledger system 440 to the pharmacist or physician.

In some aspects, rejections of prescriptions and warning issued by shared ledger system 440 may be monitored and tracked for future use in identifying likely fraudulent customers, physicians, etc. For example, if prescriptions associated with a particular patient are often received by a pharmacist with modifications, or are often received by multiple pharmacists in the same day, shared ledger system 440 may monitor this activity and may indicate or provide warnings to both the pharmacist and physician that potential abuses or fraud are occurring with their prescriptions. In addition, where prescriptions associated with a particular physician or particular pharmacist often trigger warnings in shared ledger system 440, future prescriptions associated with that physician or pharmacist may also receive heightened scrutiny or have a warning indicator associated with them that may be provided to any pharmacist that is attempting to fill the prescription or to the prescribing physician. For example, each physician and pharmacist may have an associated metric score that is generated based on prescription history where, for example, each warning due to activity by the physician or pharmacist may increase (or decrease) the metric score. Once the metric score is above (or below) a pre-determined threshold, shared ledger system 440 may permanently assign a warning and indication that manual verification should be used for any future attempts to use prescriptions associated with that particular physician or pharmacist.

Figure 7:
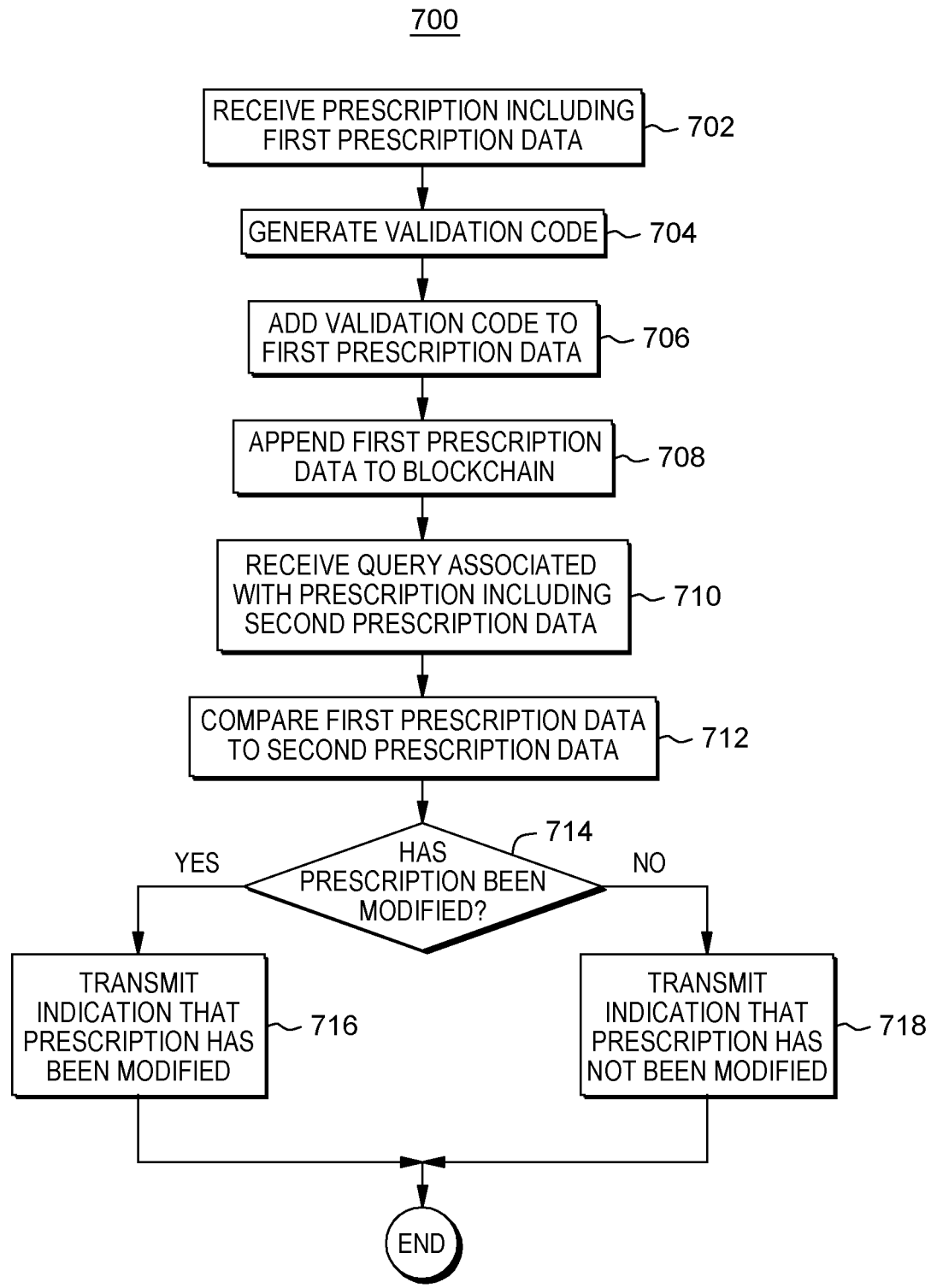
FIG. 7 is a flow chart of a method according to an embodiment of the present disclosure.

With reference now to FIG. 7, a method 700 for reducing prescription fraud through the use of a blockchain is disclosed. In some aspects, all or a portion of method 700 may be performed by various parts of the system including, for example, nodes 200, validator nodes 300, prescription entry device 402, prescription verification device 420, shared ledger system 440, or any other portion of the system.

At 702, a prescription 502 comprising first prescription data 412 is received by shared ledger system 440, e.g., at nodes 200 or validators 300, from a prescription entry device 402 associated with a prescribing entity.

At 704, a validation code for the prescription 502 based on the first prescription data 412 is generated. In some aspects, the validation code may be generated by prescription entry device 402 and submitted with the prescription 502. In some aspects, shared ledger system 440 may generate the validation code after the prescription 502 including first prescription data 412 has been received.

At 706, the validation code is added to the first prescription data, e.g., by prescription entry device 402 or shared ledger system 440. In some aspects, the validation code may be included with the prescription data 412 when the prescription data 412 is submitted by prescription entry device 402 to shared ledger system 440. In some aspects, shared ledger system 440 may add the validation code to the prescription data 412, for example, by nodes 200 or validators 300.

At 708, the first prescription data including the validation code is appended to blockchain 100, e.g., after validation has occurred and consensus has been reached by validator nodes 300.

At 710, a query associated with the prescription is received by shared ledger system 440 from a prescription verification device 420 associated with a prescription dispensing entity, e.g., a pharmacy. The query includes second prescription data. In some aspects, the query may also include the validation code. For example, the validation code may be written on or otherwise included as part of the prescription.

At 712, the first prescription data is compared to the second prescription data by shared ledger system 440. For example, shared ledger system 440 may compare the first and second prescription data to determine whether any modifications have been made to prescription 502 from the time it was created or provided by prescription entry device 402 to shared ledger system 440 until the prescription 502 was received by the prescription dispensing entity, e.g., pharmacy, and submitted with the query. As an example, the key regions of the prescription may be checked, e.g., via image processing, to determine whether a modification has been made and if so whether the combined risk weightings of the key regions is above the pre-determined risk threshold.

At 714, shared ledger system 440 determines based on the comparison whether the prescription has been modified.

At 716, in response to a determination that the prescription has been modified, shared ledger system 440 transmits to the prescription verification device an indication that the prescription has been modified. In some aspects, the indication may include an indication that manual verification of the prescription with the prescribing entity is required before dispensing the prescription.

At 718, in response to a determination that the prescription as not been modified, shared ledger system 440 transmits to the prescription verification device an indication that the prescription has not been modified.

Figure 8:
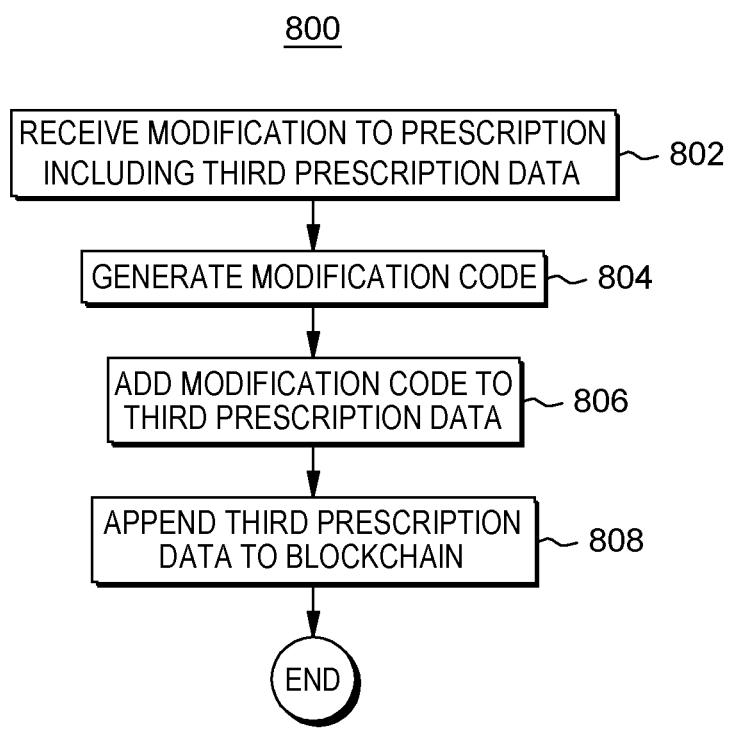
FIG. 8 is a flow chart of a method according to an embodiment of the present disclosure.

With reference now to FIG. 8, a method 800 for modifying a prescription on the shared ledger is disclosed. At 802, a modification to the prescription from method 700 is received from the prescription entry device 402 associated with the prescribing entity. The modification includes third prescription data, e.g., data showing a modification from the first prescription data. For example, the prescribing physician may make a change to the first prescription, e.g., add additional refills, etc., and may submit the modified prescription to shared ledger system 440 as third prescription data for addition to the blockchain.

At 804, a modification code is generated for the modification to the prescription, e.g., by the prescription entry device 402 or shared ledger system 440.

At 804, the validation code is added to the third prescription data.

At 806, the third prescription data including the modification code is appended to the blockchain.

Figure 9:
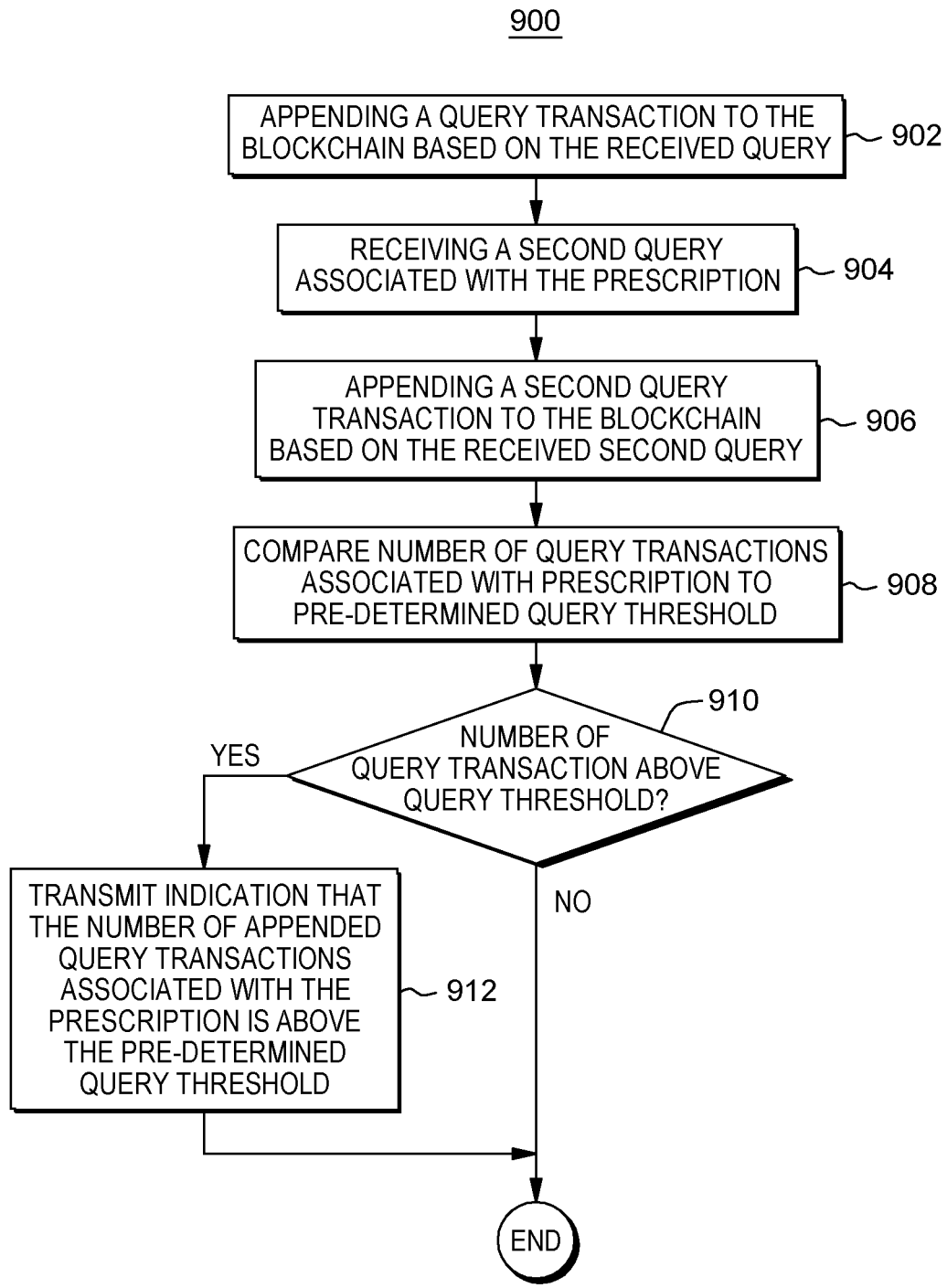
FIG. 9 is a flow chart of a method according to an embodiment of the present disclosure.

With reference now to FIG. 9, a method 900 for querying a blockchain for a prescription is disclosed. At 902, a query transaction is appended to the blockchain based on the received query from step 710 (FIG. 7).

At 904, a second query associated with the prescription is received from a second prescription verification device associated with a second prescription dispensing entity. In some aspects, the second prescription dispensing entity may be different than the prescription dispensing entity from step 710 (FIG. 7). In some aspects, the second prescription dispensing entity may be the same as the first prescription dispending entity.

At 906, a second query transaction is appended to the blockchain based on the received second query.

At 908, the number of query transactions associated with the prescription is compared to a predetermine query threshold.

At 910, shared ledger system 440 determines whether the number of appended query transactions associated with the prescription is above the pre-determined query threshold.

At 912, if shared ledger system 440 determines that the number of appended query transactions associated with the prescription is above the pre-determined query threshold, an indication is transmitted to at least one of the second prescription verification device, the first prescription verification device, and the prescription entry device, that the number of appended query transactions associated with the prescription is above the pre-determined query threshold. Otherwise, no further action is taken based on the determination.

Figure 10:
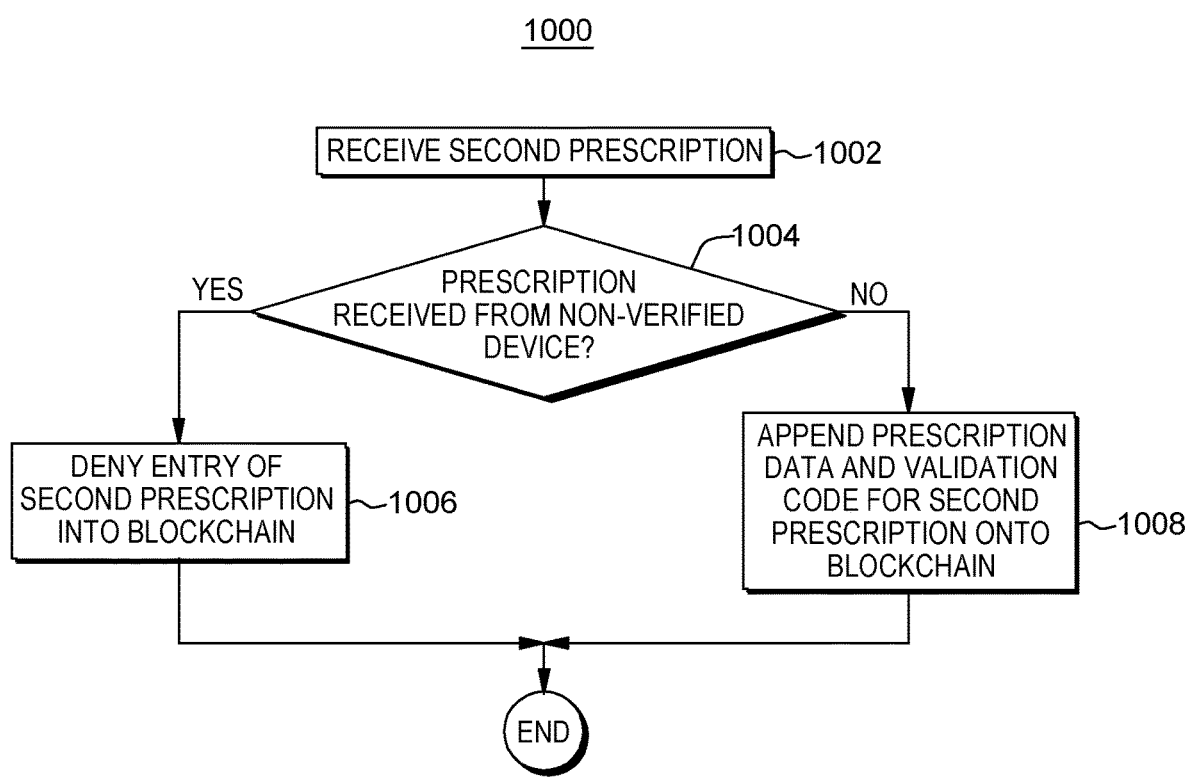
FIG. 10 is a flow chart of a method according to an embodiment of the present disclosure.

With reference now to FIG. 10, a method 1000 for denying prescriptions from non-verified devices is disclosed. At 1002, a second prescription is received by shared ledger system 440 from a second prescription entry device.

At 1004, shared ledger system 440 determines whether the second prescription entry device is a device that has been verified as belonging to a valid prescribing entity.

At 1006, if shared ledger system 440 determines that the second prescription entry device is not verified, entry of the second prescription into the blockchain 100 is denied.

At 1008, if shared ledger system 440 determines that the second prescription entry device is verified as belonging to a valid prescribing entity, the prescription data and a validation code for second prescription are appended to the blockchain according to steps 702-708 of method 700 (FIG. 7).

Figure 11:
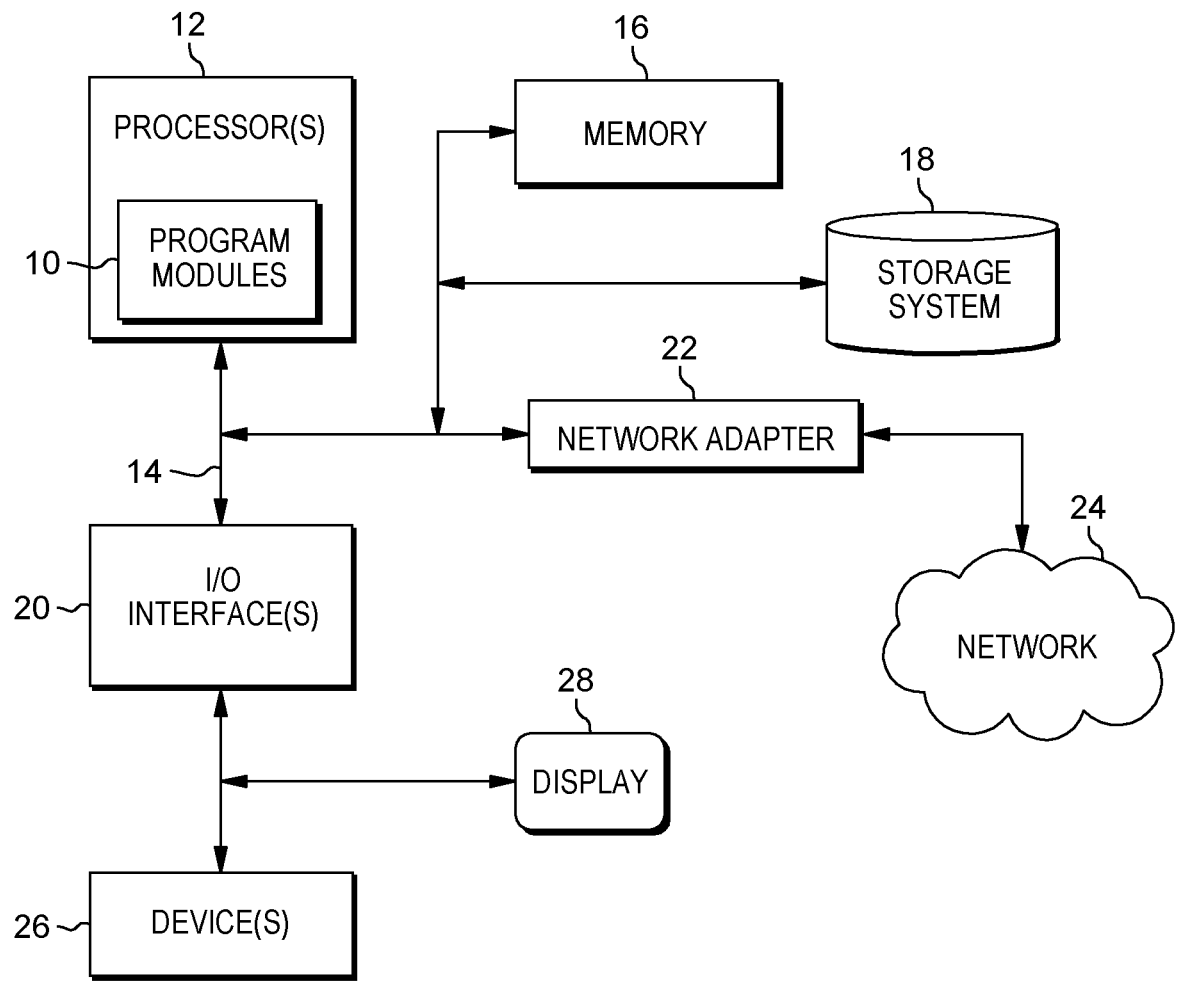
FIG. 11 is an exemplary block diagram of a computer system in which processes involved in the system, method, and computer program product described herein may be implemented.

FIG. 11 illustrates a schematic of an example computer or processing system that may implement any portion of prescription entry device 402, prescription verification device 420, shared ledger system 440, blockchain 100, nodes 200, validators 300, systems, methods, and computer program products described herein in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a software module 10 that performs the methods described herein. The module 10 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages, a scripting language such as Perl, VBS or similar languages, and/or functional languages such as Lisp and ML and logic-oriented languages such as Prolog. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The computer program product may comprise all the respective features enabling the implementation of the methodology described herein, and which—when loaded in a computer system—is able to carry out the methods. Computer program, software program, program, or software, in the present context means any expression, in any language, code or notation, of a set of instructions intended to cause a system having an information processing capability to perform a particular function either directly or after either or both of the following: (a) conversion to another language, code or notation; and/or (b) reproduction in a different material form.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Various aspects of the present disclosure may be embodied as a program, software, or computer instructions embodied in a computer or machine usable or readable medium, which causes the computer or machine to perform the steps of the method when executed on the computer, processor, and/or machine. A program storage device readable by a machine, tangibly embodying a program of instructions executable by the machine to perform various functionalities and methods described in the present disclosure is also provided.

The system and method of the present disclosure may be implemented and run on a general-purpose computer or special-purpose computer system. The terms "computer system" and "computer network" as may be used in the present application may include a variety of combinations of fixed and/or portable computer hardware, software, peripherals, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, and/or server. A module may be a component of a device, software, program, or system that implements some "functionality", which can be embodied as software, hardware, firmware, electronic circuitry, or etc.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method implemented by at least one hardware processor, comprising:
   receiving, by the at least one hardware processor, a prescription from a prescription entry device associated with a prescribing entity, the prescription comprising first prescription data for appending to a shared blockchain ledger comprising a database shared by multiple computing nodes participating in a system based on a blockchain protocol, the first prescription data comprising a first digital image of the prescription obtained from a digital scan of the prescription using an image scanning device associated with the prescribing entity, the first digital image having separate predetermined regions, each separate predetermined region having a corresponding different information content related to said prescription and each separate region having an associated different visual indication corresponding to a different risk level threshold for prescription information content modifying;
   generating, by the at least one hardware processor, a validation code for the prescription based on the first prescription data;
   adding, by the at least one hardware processor, the validation code to the first prescription data;
   appending, by the at least one hardware processor, the first prescription data including the validation code to a blockchain of the shared ledger;
   receiving, by the at least one hardware processor, a query associated with the prescription from a prescription verification device associated with a prescription dispensing entity, the query comprising second prescription data submitted to the shared ledger for appending to the blockchain, the second prescription data comprising a second digital image of the prescription, the second digital image having same predetermined regions and same associated different risk level thresholds for prescription modifying as the first prescription;
   comparing, using image processing by the at least one hardware processor at the shared ledger, the first prescription data to the second prescription data by performing, in each of the separate predetermined regions having said associated visual indication, a pixel comparison of the first digital image and the second digital image;
   determining, by the at least one hardware processor, based on the pixel comparison in each of the predetermined regions that the prescription has been modified in a predetermined region when a threshold difference between the pixels in the predetermined region of the first digital image and the pixels in a corresponding predetermined region of the second digital image has been reached;
   identifying, by the at least one hardware processor, a risk level of each separate predetermined region by its associated visual indication;
   assigning, by the at least one hardware processor, an associated weight value to each determined modification based on the identified risk level of an associated predetermined region where each of the determined modifications occur;
   combining, by the at least one hardware processor, the weighted values assigned to all of the determined modifications based on their associated predetermined regions to form a combined value;
   comparing, by the at least one hardware processor, the combined value against a pre-determined risk threshold value for said prescription; and
   responsive to determining that the combined value exceeds said pre-determined risk threshold value,
   transmitting, by the at least one hardware processor at the shared ledger, to the prescription verification device an indication that the prescription has been modified beyond the pre-determined risk threshold or otherwise transmitting to the prescription verification device an indication that the prescription has not been modified beyond the pre-determined risk threshold,
   wherein responsive to receiving the transmitted indication that the prescription has been modified beyond the pre-determined risk threshold, the prescription dispensing entity preventing a dispensing of items of said prescription, otherwise in response to the indication that the prescription has not been modified beyond the pre-determined risk threshold, the prescription dispensing entity dispensing the items of said prescription.

2. The method of claim 1, further comprising:
   receiving a modification to the prescription from the prescription entry device associated with the prescribing entity, the modification comprising to third prescription data;
   generating a modification code for the modification to the prescription;
   adding the modification code to the third prescription data; and
   appending the third prescription data including the modification code to the blockchain.

3. The method of claim 1, further comprising appending a query transaction to the blockchain based on the received query.

4. The method of claim 3, further comprising:
   receiving a second query associated with the prescription from a second prescription verification device associated with a second prescription dispensing entity;
   appending a second query transaction to the blockchain based on the received second query;
   determining that the number of appended query transactions associated with the prescription is above a pre-determined query threshold; and
   transmitting to at least one of the second prescription verification device, the first prescription verification device, and the prescription entry device, an indication that the number of appended query transactions associated with the prescription is above the pre-determined query threshold.

5. The method of claim 1, wherein transmitting to the prescription verification device the indication that the prescription has been modified includes an indication that manual validation of the prescription with the prescribing entity is required.

6. A system comprising:
at least one hardware processor performing a method to:
receive a prescription from a prescription entry device associated with a prescribing entity, the prescription comprising first prescription data for appending to a shared blockchain ledger comprising a database shared by multiple computing nodes participating in a system based on a blockchain protocol, the first prescription data comprising a first digital image of the prescription obtained from a digital scan of the prescription using an image scanning device associated with the prescribing entity, the first digital image having separate predetermined regions, each separate predetermined region having a corresponding different information content related to said prescription and each separate region having an associated different visual indication corresponding to a different risk level threshold for prescription information content modifying;
generate a validation code for the prescription based on the first prescription data;
add the validation code to the first prescription data;
append the first prescription data including the validation code to a blockchain of the shared ledger;
receive a query associated with the prescription from a prescription verification device associated with a prescription dispensing entity, the query comprising second prescription data submitted to the shared ledger for appending to the blockchain, the second prescription data comprising a second digital image of the prescription, the second digital image having same predetermined regions and same associated different risk level thresholds for prescription modifying as the first prescription;
compare using image processing at the shared ledger the first prescription data to the second prescription data by performing, in each of the separate predetermined regions having said associated visual indication, a pixel comparison of the first digital image and the second digital image;
determine based on the pixel comparison performed in each of the predetermined regions that the prescription has been modified in a predetermined region when a threshold difference between the pixels in the predetermined region of the first digital image and the pixels in a corresponding predetermined region of the second digital image has been reached;
identify a risk level of each predetermined region by its associated visual indication;
assign an associated weight value to each determined modification based on the identified risk level of an associated predetermined region where each of the determined modifications occur;
combine the weighted values assigned to all of the determined modifications based on their associated predetermined regions to form a combined value;
compare the combined value against a pre-determined risk threshold value for said prescription; and
responsive to determining that the combined value exceeds said pre-determined risk threshold value, transmit from the shared ledger to the prescription verification device an indication that the prescription has been modified beyond the pre-determined risk threshold or otherwise transmit to the prescription verification device an indication that the prescription has not been modified beyond the pre-determined risk threshold,
wherein responsive to receiving the indication that the prescription has been modified beyond the pre-determined risk threshold, the prescription dispensing entity preventing a dispensing of items of said prescription, otherwise in response to the indication that the prescription has not been modified beyond the pre-determined risk threshold, the prescription dispensing entity dispensing the items of said prescription.

7. The system of claim 6, the at least one hardware processor further configured to:
receive a modification to the prescription from the prescription entry device associated with the prescribing entity, the modification comprising to third prescription data;
generate a modification code for the modification to the prescription;
add the validation code to the third prescription data; and
append the third prescription data including the modification code to the blockchain.

8. The system of claim 6, the at least one hardware processor further configured to append a query transaction to the blockchain based on the received query.

9. The system of claim 8, the at least one hardware processor further configured to:
receive a second query associated with the prescription from a second prescription verification device associated with a second prescription dispensing entity;
append a second query transaction to the blockchain based on the received second query;
determine that the number of appended query transactions associated with the prescription is above a pre-determined query threshold; and
transmit to at least one of the second prescription verification device, the first prescription verification device, and the prescription entry device, an indication that the number of appended query transactions associated with the prescription is above the pre-determined query threshold.

10. The system of claim 6, wherein transmitting to the prescription verification device the indication that the prescription has been modified includes an indication that manual validation of the prescription with the prescribing entity is required.

11. A non-transitory computer readable medium comprising instructions that, when executed by at least one hardware processor, configure the at least one hardware processor to:
receive a prescription from a prescription entry device associated with a prescribing entity, the prescription comprising first prescription data for appending to a shared blockchain ledger comprising a database shared by multiple computing nodes participating in a system based on a blockchain protocol, the first prescription data comprising a first digital image of the prescription obtained from a digital scan of the prescription using an image scanning device associated with the prescribing entity, the first digital image having predetermined regions, each predetermined region having a corresponding different information content related to said prescription and each separate region having an associated different visual indication corresponding to a different risk level threshold for prescription information content modifying;

generate a validation code for the prescription based on the first prescription data;

add the validation code to the first prescription data;

append the first prescription data including the validation code to a blockchain of the shared ledger;

receive a query associated with the prescription from a prescription verification device associated with a prescription dispensing entity, the query comprising second prescription data submitted to the shared ledger for appending to the blockchain, the second prescription data comprising a second digital image of the prescription, the second digital image having same predetermined regions and same associated different risk level thresholds for prescription modifying as the first prescription;

compare using image processing at the shared ledger the first prescription data to the second prescription data by performing, in each of the separate predetermined regions having said associated visual indication, a pixel comparison of the first digital image and the second digital image;

determine based on the pixel comparison performed in each of the predetermined regions that the prescription has been modified in a predetermined region when a threshold difference between the pixels in the predetermined region of the first digital image and the pixels in a corresponding predetermined region of the second digital image has been reached; and identify a risk level of each predetermined region by its associated visual indication;

assign an associated weight value to each determined modification based on the identified risk level of an associated predetermined region where each of the determined modifications occur;

combine the weighted values assigned to all of the determined modifications based on their associated predetermined regions to form a combined value;

compare the combined value against a pre-determined risk threshold value for said prescription; and responsive to determining that the combined value exceeds said pre-determined risk threshold value, transmit from the shared ledger to the prescription verification device an indication that the prescription has been modified beyond the pre-determined risk threshold or otherwise transmit to the prescription verification device an indication that the prescription has not been modified beyond the pre-determined risk threshold, wherein responsive to receiving the indication that the prescription has been modified beyond the pre-determined risk threshold, the prescription dispensing entity preventing a dispensing of items of said prescription, otherwise in response to the indication that the prescription has not been modified beyond the pre-determined risk threshold, the prescription dispensing entity dispensing the items of said prescription.

12. The non-transitory computer readable medium of claim 11, the at least one hardware processor further configured to:

receive a modification to the prescription from the prescription entry device associated with the prescribing entity, the modification comprising to third prescription data;

generate a modification code for the modification to the prescription;

add the validation code to the third prescription data; and append the third prescription data including the modification code to the blockchain.

13. The non-transitory computer readable medium of claim 11, the at least one hardware processor further configured to append a query transaction to the blockchain based on the received query.

14. The non-transitory computer readable medium of claim 13, the at least one hardware processor further configured to:

receive a second query associated with the prescription from a second prescription verification device associated with a second prescription dispensing entity;

append a second query transaction to the blockchain based on the received second query;

determine that the number of appended query transactions associated with the prescription is above a pre-determined query threshold; and transmit to at least one of the second prescription verification device, the first prescription verification device, and the prescription entry device, an indication that the number of appended query transactions associated with the prescription is above the pre-determined query threshold.

15. The method of claim 1, wherein each said region of a first digital image or second digital image has a separate defined pre-determined risk threshold for modification as a percent threshold difference.

16. The system of claim 6, wherein each said region of a first digital image or second digital image has a separate defined pre-determined risk threshold for modification as a percent threshold difference.

17. The non-transitory computer readable medium of claim 11, wherein each said region of a first digital image or second digital image has a separate defined pre-determined risk threshold for modification as a percent threshold difference.

18. The method of claim 1, wherein said associated different visual indication of said separate predetermined regions is selected from the group consisting of: different colors, different shadings or different patterns.

19. The system of claim 6, wherein said associated different visual indication of said separate predetermined regions is selected from the group of: different colors, different shadings or different patterns.

20. The non-transitory computer readable medium of claim 11, wherein said associated different visual indication of said separate predetermined regions is selected from the group of: different colors, different shadings or different patterns.

* * * * *